United States Patent
Durandis

(10) Patent No.: US 9,339,351 B2
(45) Date of Patent: May 17, 2016

(54) ADJUSTABLE DENTAL SPACER

(71) Applicant: Kenny Durandis, Brockton, MA (US)

(72) Inventor: Kenny Durandis, Brockton, MA (US)

(*) Notice: Subject to any disclaimer, the term of this patent is extended or adjusted under 35 U.S.C. 154(b) by 0 days.

(21) Appl. No.: 14/016,067

(22) Filed: Aug. 31, 2013

(65) Prior Publication Data

US 2015/0064650 A1 Mar. 5, 2015

(51) Int. Cl.
*A61C 7/00* (2006.01)
*A61C 7/18* (2006.01)

(52) U.S. Cl.
CPC .... *A61C 7/00* (2013.01); *A61C 7/18* (2013.01)

(58) Field of Classification Search
CPC ................................... A61C 7/18; A61C 5/12
USPC .................................................... 433/23, 148
See application file for complete search history.

(56) References Cited

U.S. PATENT DOCUMENTS

| | | | | | |
|---|---|---|---|---|---|
| 957,032 | A | * | 5/1910 | Brady | 433/23 |
| 2,502,902 | A | * | 4/1950 | Tofflemire | 606/54 |
| 3,127,677 | A | * | 4/1964 | Schachter | 433/17 |
| 5,151,027 | A | * | 9/1992 | Mann | 433/1 |
| 5,647,743 | A | * | 7/1997 | Schmitt | 433/23 |

FOREIGN PATENT DOCUMENTS

DE 195 01 648 C1 * 2/1996

* cited by examiner

*Primary Examiner* — Ralph Lewis
(74) *Attorney, Agent, or Firm* — Dunlap, Bennett & Ludwig PLLC

(57) ABSTRACT

A dental spacer that is adjustable and attaches to a tooth. The dental spacer may include a ring with an inner surface and an outer surface. A screw may be secured to the ring to compress and expand the ring size. A spacer may be attached to the outer surface of the ring and may abut against an adjacent tooth. Therefore, the space between two teeth adjacent to a removed tooth may be preserved.

10 Claims, 3 Drawing Sheets

ADJUSTABLE DENTAL SPACER

BACKGROUND OF THE INVENTION

The present invention relates to a dental spacer and, more particularly, to an apparatus called adjustable dental spacer that may be secured to a tooth to maintain eruption space for a permanent tooth or teeth to erupt following the extraction of a baby tooth or teeth.

A dental extraction (also referred to as exodontia) is the removal of a tooth from the mouth. Currently, to maintain eruption space for one or more succedaneous (permanent) teeth when one or more deciduous (baby)teeth have to be extracted, an impression must be taken, a mold formed and sent to a dental lab for one or two weeks for an appliance fabrication. Therefore, multiple appointments must be scheduled within a short time frame to avoid or before adjacent teeth drift into the empty space where the dental extraction was done. Further, error may occur in the impression taking process causing the fabricated space maintainer to be ill-fitting, forcing further appointments and time wasted. Also, in the time required for appliance fabrication and appointing the patient, adjacent teeth may drift into the eruption space, in which case even a properly fabricated spacer will not fit.

As can be seen, there is a need for an apparatus like the fully-adjustable dental spacer that does not require off-site fabrication and allows immediate installation of the appliance and in situ adjustment the very day the dental extraction was performed to prevent drifting teeth.

SUMMARY OF THE INVENTION

In one aspect of the present invention, a dental spacer comprises: an adjustable ring made of thin stainless steel band; comprising an inner surface and an outer surface, wherein the ring is formed to be secured around a tooth; an adjusting screw block, the adjusting screw block disposed on the outside of the ring; and adjusting screw, the adjusting screw configured to engage the adjusting screw block and selectively adjust the circumference of the ring; a spacer housing, the spacer housing on the proximal side of the adjusting screw block; and a spacer, the spacer is adjustable and is to be inserted into the spacer housing on one end and touch the non-attachment tooth on the other end of the empty space left by the extracted tooth or teeth.

In another aspect of the present invention, a method of installing a spacer device comprises: placing an adjustable ring onto an attachment tooth adjacent to a tooth that has been removed; tightening the adjustable ring to the attachment tooth by turning the adjusting screw; measuring the distance between the attachment and non-attachment teeth, inserting the spacer into the spacer housing and securing it in place.

These and other features, aspects and advantages of the present invention will become better understood with reference to the following drawings, description and claims.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides a method and apparatus for maintaining eruption space. It is a dental spacer that is fully adjustable and attaches to a tooth. The dental spacer may include a ring configures as a thin band, an adjusting screw block on the outside surface of the ring, an adjusting screw that engages the screw block and adjusts the circumference of the ring by expanding or shrinking the ring size, a spacer housing and a spacer on an end of the adjusting screw block. As the spacer is attached to the outer surface of the ring and inserted and secured in the spacer housing and touching the non-attachment adjacent tooth, the space between two teeth where the extracted tooth was may be preserved.

The present invention may include an adjustable, one-size fits all, ring and spacer device capable of maintaining eruption space for one or more succedaneous teeth, when one or more deciduous teeth have to be extracted without subjecting the patient to the discomfort of taking a dental impression. The present invention may be placed immediately after dental extraction while the patient is still anesthetized to avoid discomfort to the patient and conserve maximum eruption space. The present invention may be prefabricated, and the components may be fully adjustable to fit any primary or permanent molars to cover the size of the eruption space.

Figure 1:
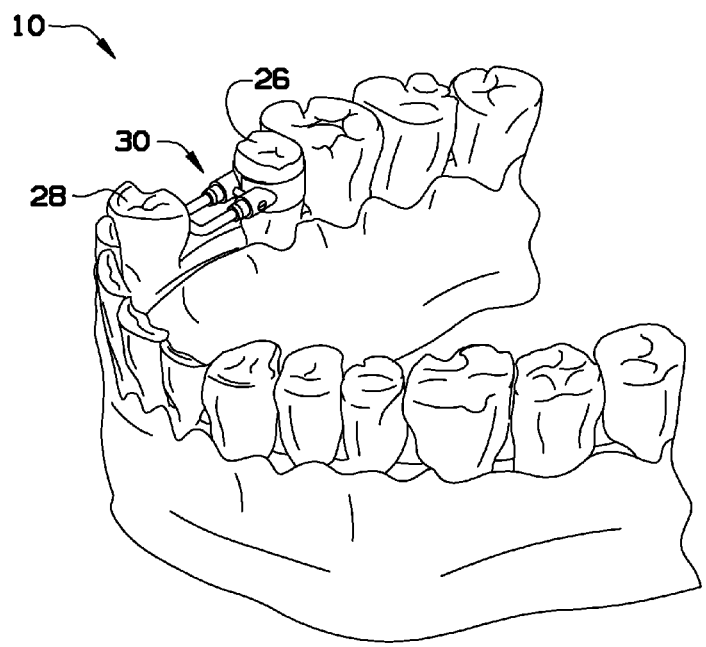
FIG. 1 is a perspective view of the present invention.
Figure 2:
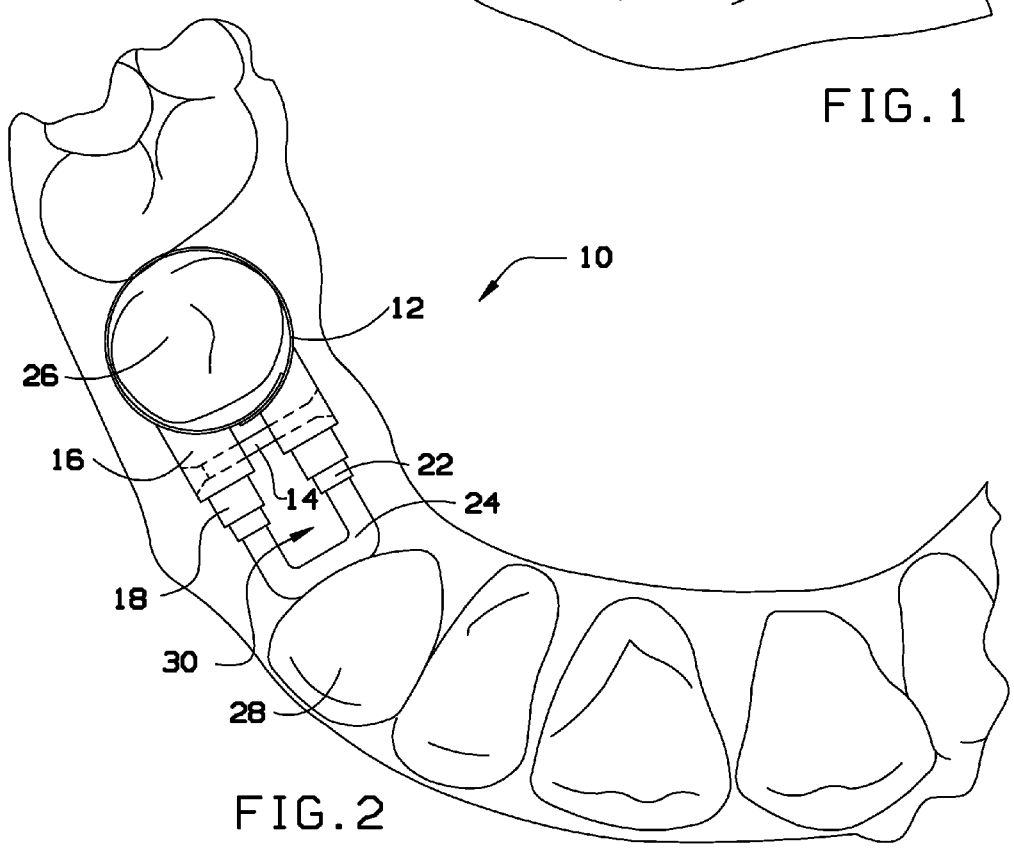
FIG. 2 is a perspective view of the present invention shown in use.
Figure 3:
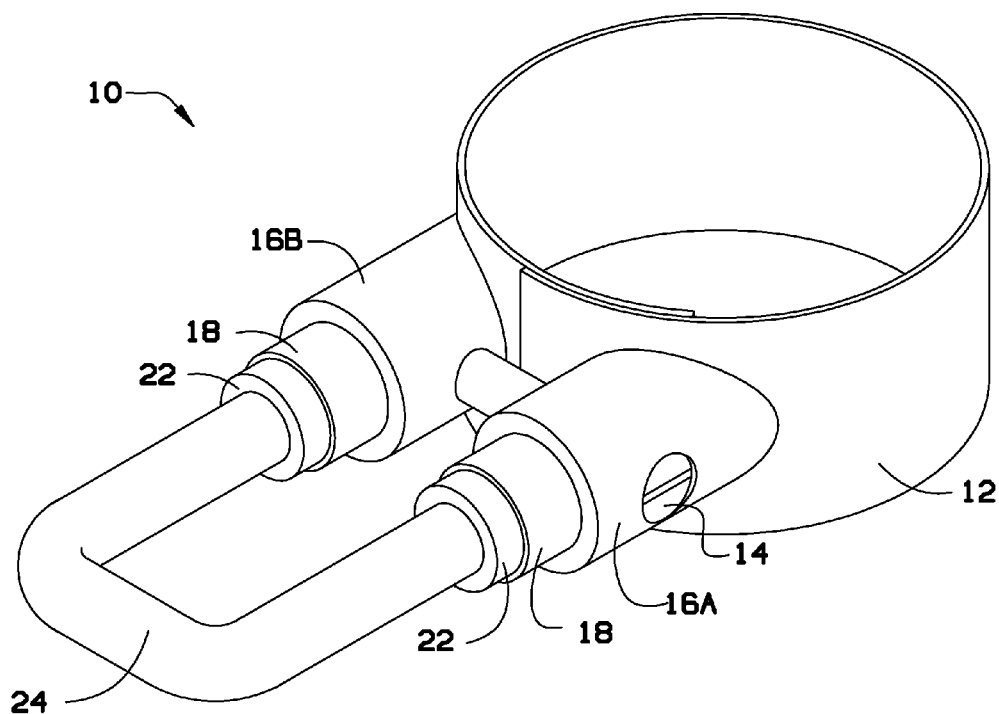
FIG. 3 is a top view of the present invention shown in use.
Figure 4:
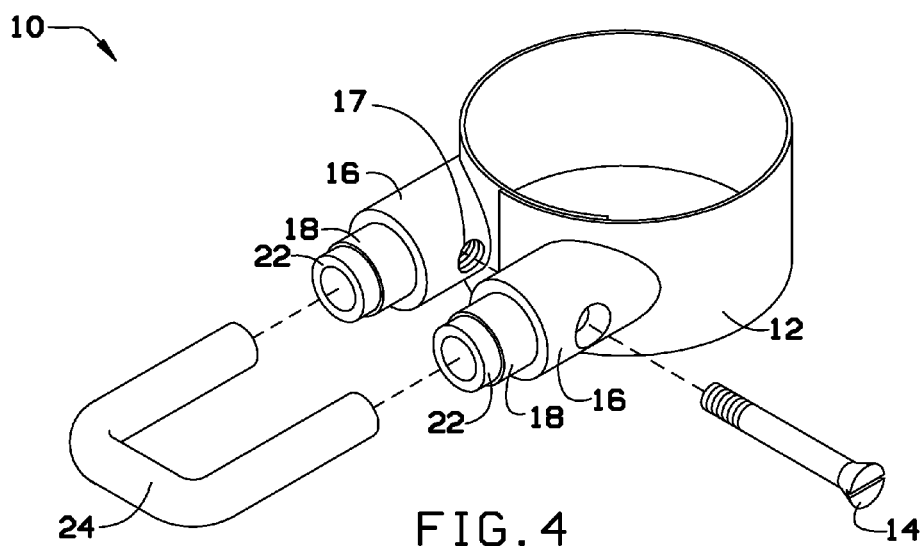
FIG. 4 is an exploded view of the present invention.
Figure 5:
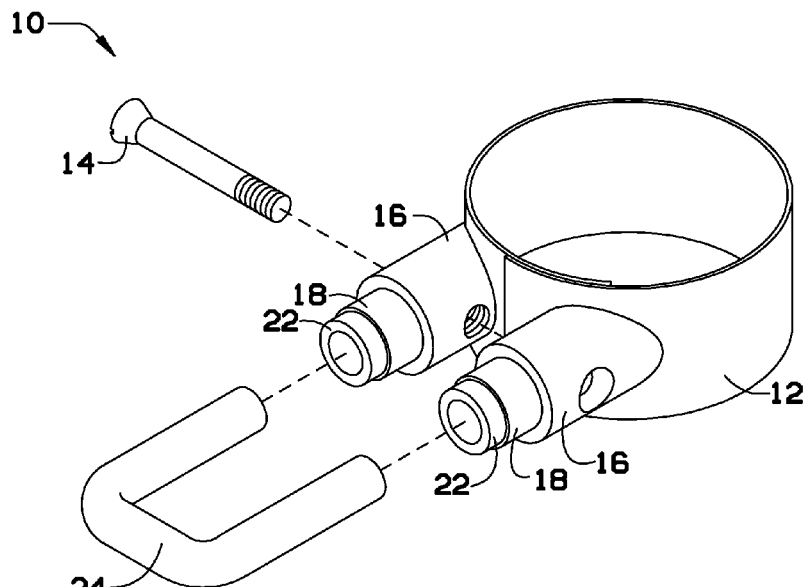
FIG. 5 is an exploded view of the present invention demonstrating an alternative assembly.
Figure 6:
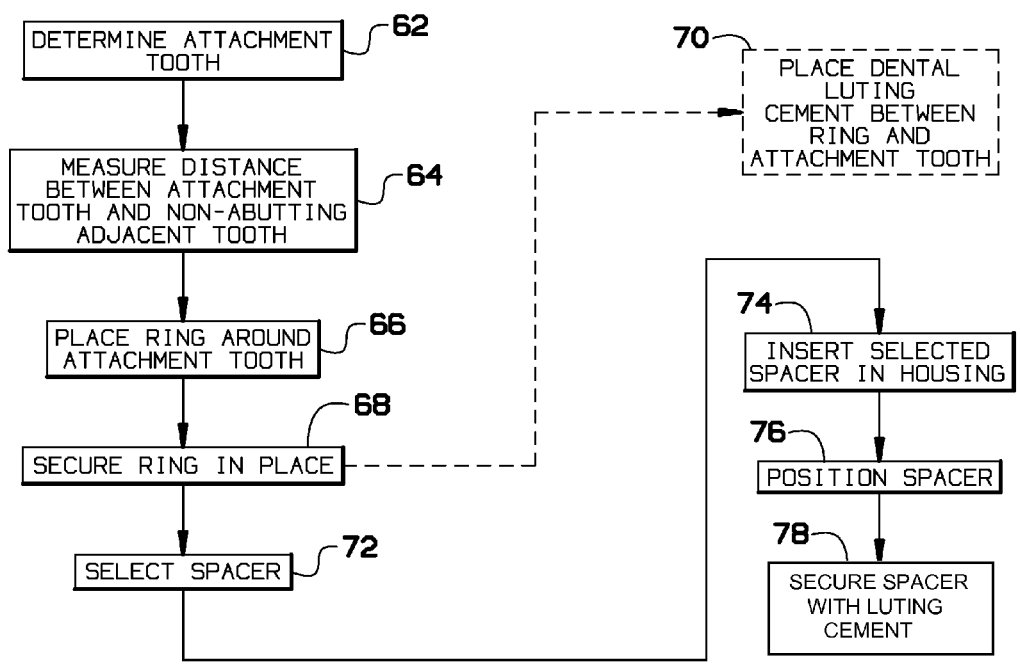
FIG. 6 is a flowchart describing a method of using the present invention.

Referring to FIGS. 1 through 5, the present invention may include a dental spacer 10. The dental spacer 10 may include an adjustable ring 12. The adjustable ring 12 may include an inner surface and an outer surface. The ring 12 is formed to be secured around a tooth 26. A spacer 24 may be attached to a spacer housing from the outer surface of the ring 12. The spacer 24 may be substantially perpendicular to the outer surface of the ring 12. When the dental spacer 10 is placed on the tooth 26, the dental spacer 10 may prevent the drifting of the adjacent teeth 26, 28 into the eruption space 30 when a primary tooth is removed.

In certain embodiments, the ring 12 of the present invention may attach to the adjacent tooth 26 that may be the strongest and/or may have the longest time frame until exfoliation. The ring 12 may be a flat piece of stainless steel that may have a thickness of about 0.15 mm and a width of about 5 mm. The ring 12 of the present invention may include a first end and a second end bent into a circle. The first end may overlap the second end.

In certain embodiments, the present invention may further include adjusting screw blocks 16 to house and secure the spacer 24. The adjusting screw blocks 16 may include a first adjusting screw block 16a and a second adjusting screw block 16b. The first adjusting screw block 16a may be attached to the outer surface of the ring 12 near the first end and the second adjusting screw block 16b may be attached to the outer surface of the ring 12 near the second end. The first adjusting screw block 16a may include an opening therethrough. The second adjusting screw block 16b may include a threaded opening 17. A screw 14 may pass through the opening of the first adjusting screw block 16a and may screw into the threaded portion 17. When the screw 14 is tightened the ring 12 may be compressed, and when the screw 14 is loosened the ring 12 may expand.

In certain embodiments, the spacer 24 of the present invention may be attached to the ring 12 by attaching to the adjusting screw blocks 16. In such embodiments, the adjusting screw blocks 16 may include a spacer housing 18 to receive and secure the spacer 24. In certain embodiments, the spacer housing 18 may further include two hollow ends 22 so that when the spacer 24 is placed within the spacer housing 18, the spacer 24 may be secured to the adjusting screw blocks 16. In certain embodiments, dental luting cement may secure the spacer 24 to the adjusting screw blocks 16.

The spacer 24 of the present invention may be a wire with a first end and a second end. The wire may be bent so that the first end fits within the spacer housing 18 of the first adjusting screw block 16a and the second end fits within the spacer housing 18 of the second adjusting block 16b. In certain embodiments, the spacer 24 may be made of 14 gauge stainless steel wire bent into a similar shape as a stapler.

The spacer 24 may further be designed to engage the adjusting screw 14, so that when the ring 12 closes around the tooth 26, the spacer 24 may extend and adjust to abut against the opposite adjacent tooth snuggly. This would effectively make the device capable of regaining eruption in the primary and mixed dentition and distalize the tooth to regain space in the permanent dentition where drifting has already occurred. In alternative embodiments, the spacer 24 may be made of a ridgelap shaped wire mesh upon which an acrylic tooth may be built to turn the device into a temporary tooth replacement and prevent over eruption of the opposing tooth.

A method of using the invention may include the following. First, the attachment tooth may be determined 62. Then, the distance between the attachment tooth and the non-abutting adjacent tooth may be measured 64. The ring may be placed around the attachment tooth 66 and secured in place 68 by simply tightening the screw until resistance is met and the ring fits on the attachment tooth snuggly. In certain embodiments, a dental luting cement may be placed in between the ring and the attachment tooth 70 to secure the ring further. Use the distance measured to create a spacer, such as cutting the spacer using a wire cutter. Then, insert the open ends of space into the spacer housing 74, and position the spacer 76 so that spacer is touching the proximal end of the non abutting adjacent tooth. Using a dental luting cement, secure both ends of the spacers into the hollow end of the spacer housing 78.

It should be understood, of course, that the foregoing relates to exemplary embodiments of the invention and that modifications may be made without departing from the spirit and scope of the invention as set forth in the following claims.

What is claimed is:

1. A dental spacer comprising:
a ring formed of a thin band having a first end opposite a second end, wherein the first end overlaps the second end, wherein the ring comprises an inner surface and an outer surface, wherein the ring is securable around a tooth;
an adjuster comprising a first adjusting block attached near the first end of the outer surface of the ring and a second adjusting block attached near the second end of the outer surface of the ring, wherein the first adjusting block and the second adjusting block each comprise a spacer housing, wherein the adjuster is operable to adjust a circumference of the ring; and
a spacer secured within and protruding from the spacer housing of the first adjustment block and the second adjustment block.

2. The dental spacer of claim 1, wherein the spacer is substantially perpendicular to the outer surface of the ring.

3. The dental spacer of claim 1, wherein the first adjusting block comprises an opening therethrough and the second adjusting block comprises an opening comprising a threaded portion, wherein a screw is formed to pass through the first adjusting block opening and into the threaded portion of the second adjusting block, wherein the screw is tightened and loosened to adjust the circumference of the ring.

4. The dental spacer of claim 3, wherein the spacer comprises a wire having a first end and a second end, wherein the wire is bent so that the first end fits within the spacer housing of the first adjusting block and the second end fits within the spacer housing of the second adjusting block.

5. The dental spacer of claim 4, wherein the spacer housing further comprises two hollow ends to secure the spacer to the housing.

6. The dental spacer of claim 4, further comprising luting cement securing the spacer to the spacer housing.

7. A method of installing a spacer device comprising:
providing a dental spacer comprising:
a ring formed of a thin band having a first end opposite a second end, wherein the ring comprises an inner surface and an outer surface; and
an adjuster comprising a first adjusting block attached near the first end of the outer surface of the ring and a second adjusting block attached near the second end of the outer surface of the ring, wherein the first adjusting block and the second adjusting block each comprise a spacer housing,
placing the ring onto an attachment tooth adjacent to a tooth that has been removed so that the first end overlaps the second end;
tightening the first adjusting block and the second adjusting block together, thereby tightening the ring to the attachment tooth;
forming a spacer having a length to be secured to the ring and to abut the opposite tooth adjacent to the tooth that has been removed; and
inserting the spacer into the spacer housing of the first adjusting block and the second adjusting block.

8. The method of installing the spacer of claim 7, wherein the first adjusting block and the second adjusting block are tightened together by a screw.

9. The method of claim 7, further comprising measuring the distance between the teeth adjacent to the removed tooth.

10. The method of claim 7, further comprising securing the spacer in the spacer housing using dental luting cement.

* * * * *